(12) United States Patent
Kinnunen et al.

(10) Patent No.: US 8,768,445 B2
(45) Date of Patent: Jul. 1, 2014

(54) ELECTRONIC DEVICE AND METHOD FOR DETERMINING A FAT BURNING THRESHOLD USING HEART RATE VARIABILITY

(75) Inventors: Hannu Kinnunen, Oulu (FI); Juuso Nissilä, Ii (FI); Tero Posio, Oulu (FI); Ulla Salmi, Oulu (FI)

(73) Assignee: Polar Electro Oy, Kempele (FI)

( * ) Notice: Subject to any disclaimer, the term of this patent is extended or adjusted under 35 U.S.C. 154(b) by 1145 days.

(21) Appl. No.: 12/328,983

(22) Filed: Dec. 5, 2008

(65) Prior Publication Data

US 2009/0156944 A1    Jun. 18, 2009

(30) Foreign Application Priority Data

Dec. 14, 2007   (FI) .................................... 20075908

(51) Int. Cl.
    *A61B 5/0402* (2006.01)
    *A61B 5/0205* (2006.01)
    *A61B 5/024* (2006.01)
    *A61B 5/00* (2006.01)
    *A63B 24/00* (2006.01)

(52) U.S. Cl.
    CPC ........... *A61B 5/02405* (2013.01); *A61B 5/4866* (2013.01); *A63B 2230/062* (2013.01); *A63B 2024/0068* (2013.01); *A63B 2230/75* (2013.01)
    USPC ........................................ 600/519; 600/520

(58) Field of Classification Search
    USPC ....................................................... 600/520
    See application file for complete search history.

(56) References Cited

U.S. PATENT DOCUMENTS

| | | | |
|---|---|---|---|
| 5,297,558 A | 3/1994 | Acorn et al. | |
| 6,104,947 A | 8/2000 | Heikkila et al. | |
| 6,540,686 B2 * | 4/2003 | Heikkila et al. | 600/483 |
| 6,554,776 B1 | 4/2003 | Snow et al. | |
| 2003/0013995 A1 * | 1/2003 | Oshima et al. | 600/587 |
| 2009/0192391 A1 * | 7/2009 | Lovitt et al. | 600/483 |

FOREIGN PATENT DOCUMENTS

| | | | |
|---|---|---|---|
| EP | 1127542 A2 | 8/2001 | |
| EP | 1431879 A2 | 6/2004 | |
| EP | 1852062 A1 | 11/2007 | |
| WO | WO9620641 A1 | 7/1996 | |

OTHER PUBLICATIONS

B. Ashbaugh, "Fat Burning Cardio Workouts with Heart Rate Monitors", URL:http://web.archive.org/web/20070328200217/http:/www.articlecity.com/articles/health/article_4963.shtml, (published on the Internet on Mar. 28, 2007).

* cited by examiner

*Primary Examiner* — Kennedy Schaetzle
(74) *Attorney, Agent, or Firm* — Hoffmann & Baron, LLP

(57) ABSTRACT

There is provided electronic device, comprising: a receiving unit configured to receive heart rate data generated by a heart rate measuring system; a calculation unit configured to calculate heart rate variation data on the basis of the received heart rate data. The electronic device further comprises: a processing unit configured to analyse the calculated heart rate variation data in comparison with the corresponding heart rate data, and to determine at least one threshold value for fat burning on the basis of the analysis.

22 Claims, 4 Drawing Sheets

ELECTRONIC DEVICE AND METHOD FOR DETERMINING A FAT BURNING THRESHOLD USING HEART RATE VARIABILITY

CROSS-REFERENCE TO RELATED APPLICATION

This application claims priority based on Finnish Patent Application No. 20075908, filed Dec. 14, 2007, which is incorporated herein by reference.

BACKGROUND OF THE INVENTION

Field of the Invention

The invention relates to an electronic device, to a method and to a computer-readable distribution medium encoding a computer program of instructions for executing a computer process.

Description of the Related Art

Many heart rate monitor users exercise for weight control reasons and many exercise for reasons related to sustaining/improving one's fitness. It is common that users lack knowledge of the correct intensity level for exercising when considering their personal objectives. Further, one's physical condition varies on a daily basis and users lack knowledge related to the effects of their current physical condition on choosing the optimal intensity level for the exercise.

Further, information on the fat percentage or amount of fat as part of energy substrate consumption used for the exercise is often needed. Known methods of estimating fat burning as part of energetic of an exercise are based on the correlation between fat burning and the heart rate. However, fat burning is not a simple or stable characteristic that is bound to a specific intensity level but it varies greatly regardless of sex or personal fitness level, for instance. Also the consumption of fat as an energy source varies on a personal level daily and/or between the exercises. Accordingly, more accurate and effective techniques for estimating fat burning are needed.

SUMMARY OF THE INVENTION

An object of the present invention is to provide an improved method, an electronic device, and a computer-readable distribution medium. The objects of the invention are achieved by a method and an electronic device that are characterized by what is stated in the independent claims.

According to an aspect of the invention, there is provided an electronic device comprising: a receiving unit configured to receive heart rate data generated by a heart rate measuring system; and a calculation unit configured to calculate heart rate variation data on the basis of the received heart rate data. The electronic device further comprises: a processing unit configured to analyse the calculated heart rate variation data in comparison with the corresponding heart rate data, and to determine at least one threshold value for fat burning on the basis of the analysis.

According to another aspect of the invention, there is provided a method comprising: receiving heart rate data generated by a heart rate measuring system; calculating heart rate variation data on the basis of the received heart rate data; analysing the calculated heart rate variation data in comparison with the corresponding heart rate data, and determining at least one threshold value for fat burning on the basis of the analysis.

According to another aspect of the invention, there is provided a computer-readable distribution medium encoding a computer program of instructions for executing a computer process, the process comprising: receiving heart rate data generated by a heart rate measuring system; and calculating heart rate variation data on the basis of the received heart rate data. The process further comprises: analysing the calculated heart rate variation data in comparison with the corresponding heart rate data, and determining at least one threshold value for fat burning on the basis of the analysis.

The invention is based on estimating one or more threshold values for fat burning on the basis of the correlation between heart rate data and heart rate variation data.

The electronic device and method of the invention provide several advantages. Reliable information on exercise levels of a user are provided. Personal characteristics of a user are taken into account in the analysis. Thus, it is easy determine whether the exercise performance of a specific user corresponds to his/her personal goals to be achieved.

BRIEF DESCRIPTION OF THE DRAWINGS

In the following the invention will be described in greater detail with reference to the embodiments and the accompanying drawings, in which.

DETAILED DESCRIPTION OF THE PREFERRED EMBODIMENTS

Figure 1:
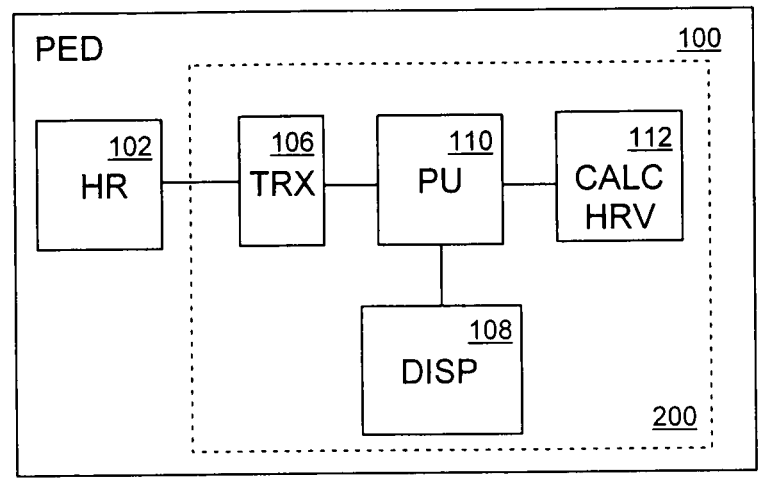
FIG. 1 shows an example of a structure of an arrangement according to an embodiment.

With reference to FIG. 1, we now examine an example of an arrangement to which embodiments of the invention can be applied. The embodiments are, however, not restricted to this arrangement described only by way of example, but a person skilled in the art can apply the instructions to other arrangements containing corresponding characteristics.

The different elements of the arrangement 100 of FIG. 1 may be separate devices that can communicate with one or more other elements of the arrangement. The arrangement 100, such as a portable electronic device, comprises a heart rate measuring unit 102, a receiving unit 106, a processing unit 110, a calculation unit 112, and a display 108.

Figure 3:
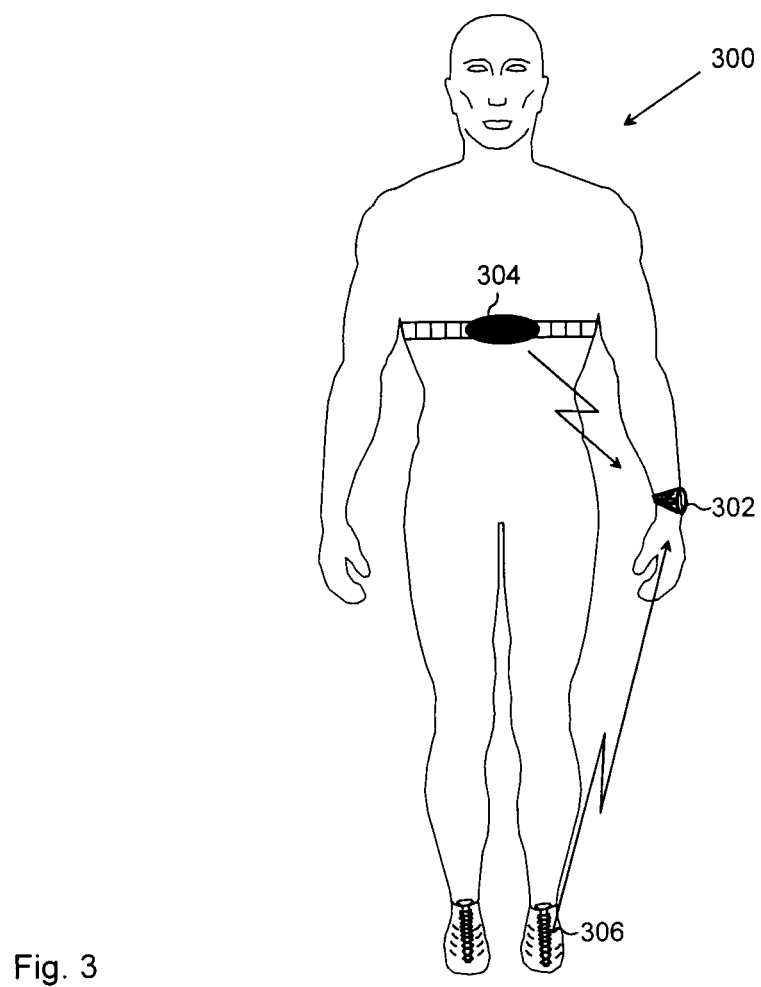
FIG. 3 shows an example of an electronic device according to an embodiment.

In an embodiment, the heart rate measuring unit 102 may comprise or be a part of a wrist device, which may be the wrist device 302 of a heart rate/performance monitor shown in FIG. 3. A heart rate monitor may comprise not only the wrist device 302, but also one or more auxiliary devices 304, 306, such as a motion sensor 306 fastened to a limb of the user 300 of the device in addition to a pulse transmitter 304 indicating electric pulses induced by the heart. The auxiliary device 304, 306 may communicate with the wrist device 302 over wired or wireless connections.

The receiving unit 106 is configured to receive heart rate data measured by the heart rate measuring unit 102. The heart rate is used here to describe the frequency of the cardiac cycle.

The heart rate may be calculated as the number of contractions, i.e. heart beats, of the heart in one minute. Any known measuring techniques can be used to measure the heart rate data.

The processing unit 110 comprises a digital signal processor and executes a computer process according to encoded instructions stored in a memory. The processing unit 110 may be implemented by using analog circuits, ASIC circuits (Application Specific Integrated Circuit), a digital processor, a memory and computer software. The processing unit 110 may constitute a part of the computer of the wrist device 302, for example.

In an embodiment, the calculation unit 112 is configured to calculate heart rate variation data on the basis of the received heart rate data. Heart rate variation (HRV) is a measure of variation in the heart rate. Heart rate variation may be calculated by analysing the time series of beat-to-beat intervals from heart rate data measured by a heart rate monitor, for example. There are various known mathematical methods of calculating heart rate variation and any of these may be used in the context of the embodiments.

In an embodiment, the processing unit 110 is configured to analyse the calculated heart rate variation data in comparison with the corresponding heart rate data, and to determine at least one threshold value for fat burning on the basis of the analysis.

In an embodiment, the determined at least one threshold value is at least one of: a heart rate value at a certain fat burning value, a heart rate variation value at a certain fat burning value, an upper limit at which fat burning is effective, a lower limit at which fat burning ends, a limit where fat burning starts, a percentage of the maximum fat burning ability at a certain heart rate variation level.

In an embodiment, the processing unit 110 may be configured to determine the threshold value at which fat burning ends on the basis of the analysis.

In an embodiment, the processing unit 110 may be configured to determine a ratio between carbohydrate consumption and fat burning on the basis of the analysis.

In an embodiment, the processing unit 110 may be configured to determine the proportion of energy that has been burned as fat on the basis of the analysis.

In an embodiment, the processing unit 110 may be configured to estimate a value where the maximum amount of fat is burned on the basis of the analysis.

In an embodiment, the processing unit 110 may be configured to estimate the value where the maximum amount of fat is burned by selecting a heart rate variation value from a heart rate variation curve.

The processing unit 110 may be further configured to provide instructions on indicating about the determined at least one threshold value on a display unit 108. The display unit 108, which may contain LCD (Liquid Crystal Display) components, for instance, may indicate the determined data graphically and/or numerically to the user 300.

Figure 2:
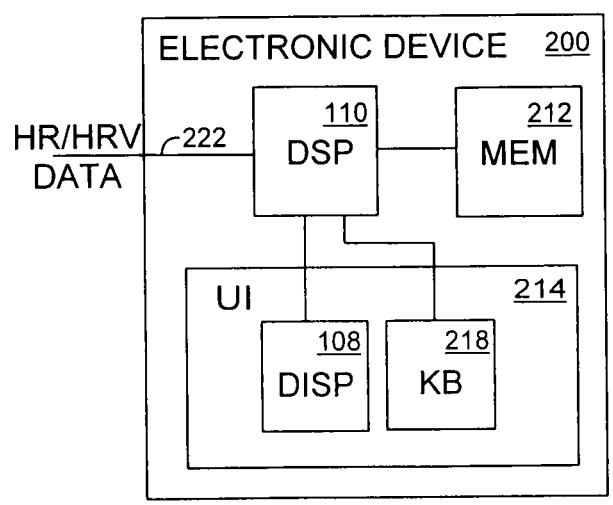
FIG. 2 shows an example of the structure of an electronic device according to an embodiment.

FIG. 2 shows another example of the structure of an electronic device 200 according to an embodiment. The electronic device 200 typically comprises a processing unit 110, a memory unit 212, and user interface parts 214, such as a display unit 108 and a keyboard 218. The electronic device 200 may be, for example, a personal computer, a wrist device 302 or a device carried on a bicycle.

The processing unit 110 controls the functions of the electronic device 200 and it may execute computer processes according to encoded instructions stored in the memory unit 212. The calculation unit 112 of FIG. 1 may be a part of the processing unit 110.

In an embodiment, the processing unit 110 is configured to analyse the received heart rate variation data 222 in comparison with the corresponding heart rate data 222, and to determine at least one threshold value for fat burning on the basis of the analysis.

In an embodiment, the processing unit 110 is configured to provide instructions on indicating about at least one of: reaching the threshold value, staying below the threshold value, remaining above the threshold value, remaining in the vicinity of the threshold value.

The threshold value, for example a heart rate value, is detected on the basis of changes in the heart rate variation. Here, the heart rate variation means temporal variations in heart beats around the expected moments at which the heart should beat. In an embodiment, the variation may be calculated as moving standard deviation, but it can also be calculated by another prior art mathematical method, e.g. by a method which utilizes the distribution function between the heart rate and the heart rate variation. Other generally used variation-measuring units are spectrum calculation power values, the maximum value of the variation, and the height of the deviation diagram.

Variations around the average heartbeat rate level occur constantly in the heartbeat rate due to the variation in the sympathetic-parasympathetic balance of the autonomic nervous system. The variation in the heartbeat rate is caused by the function of the cardiovascular control system. The main reasons for the variation are respiratory arrhythmia, variation caused by blood pressure control, and variation caused by the heat balance control of the system. Among these, the most significant one and causing the greatest variation is respiratory arrhythmia. The transmitting nervous systems of the heartbeat rate variation can be distinguished by means of a heartbeat rate variation frequency analysis.

In increasing the exertion level from the resting level, the para-sympathetic tonus decreases at first by degrees. When the heart rate level has reached a level of about 100 pulsations/min, i.e. to about 56% of the maximum heartbeat rate, the sympathetic activity starts to increase, and will have a significant effect on the heartbeat rate frequency at a level of about 63% of the maximum heartbeat rate. With low exertion, an increase in the heartbeat rate is almost completely due to decreased parasympathetic activity. The heart rate variation thus decreases in direct proportion to the disappearance of the para-sympathetic control. It is only on a higher exertion level that the sympathetic nervous system participates in controlling the heartbeat rate level with the parasympathetic one.

Figure 4:
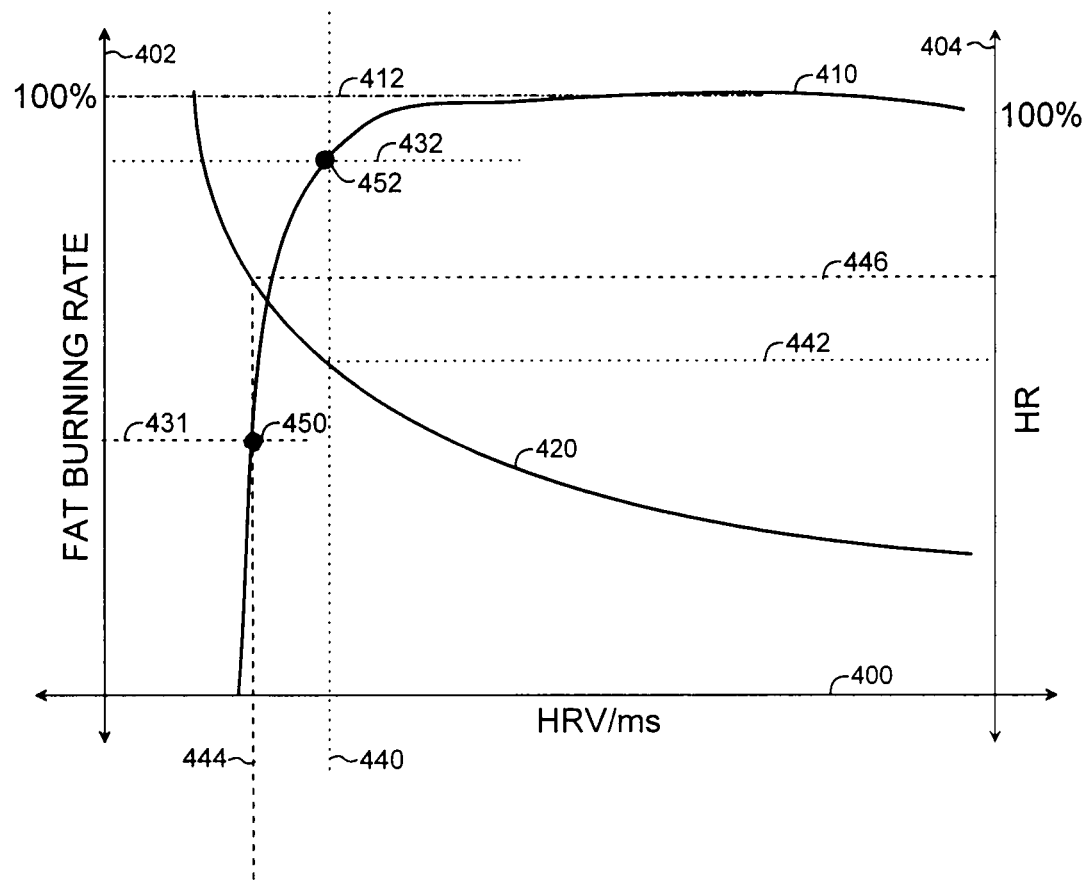
FIG. 4 illustrates an example of the relation between the heart rate and heart rate variation graphs.

As a function of heart rate, the heart rate variation naturally decreases as the heart rate, i.e. the heart beat frequency, increases. FIG. 4 illustrates the correlation between the heart rate and heart rate variation. FIG. 4 illustrates the dependency between the heart rate variation and the heart rate, which applies to the majority of people. It can be seen from FIG. 4 that as the heart rate level approaches the maximum heart rate, the heart rate variation decreases considerably.

With reference to FIG. 4, fat burning may be illustrated with a fat burning rate curve 410, which is presented as a function of heart rate variation (HRV) shown by the x-axis 400. The fat burning rate may be expressed as a percentage of the maximum fat burning rate 412 of an individual. In an embodiment, the fat burning rate is expressed as an absolute measure. The left-most y-axis 402 of FIG. 4 represents the fat burning rate and the rightmost y-axis 404 of FIG. 4 represents the heart rate.

The heart rate (HR) associated with the heart rate variation is also shown as a percentage of a person's maximum heart rate. In an embodiment, the heart rate is expressed in an absolute heart rate scale. FIG. 4 illustrates an example of a heart rate curve 420.

The association between the heart rate variation, the fat burning rate and the heart rate may be based on a personal measurement or a statistical analysis of a population studied. The association may further depend on a user parameter, such as gender, age and/or fitness level of the user.

FIG. 4 further shows statistically significant threshold values 431 (threshold 1) and 432 (threshold 2), which divide the total energy consumption into carbon hydrate oxidation and fat oxidation, i.e. fat burning in a statistically known ratio.

In an embodiment, the threshold 432 is an 80% threshold indicating that the person's fat burning rate is 80% of the person's maximum fat burning rate. This fat burning rate is obtained at a corresponding heart rate variation 440 (HRV at threshold 2) and the heart rate 442 (HR at threshold 2).

In an embodiment, the threshold is a fat burning ending threshold 450 (threshold 1), which indicates the end of fat burning. The ending fat burning rate is obtained at the corresponding heart rate variation 444 (HRV at threshold 1) and the heart rate 446 (HR at threshold 1).

In an embodiment, the fat burning rate and the corresponding heart rate variation and the heart rate are different for men and women at the fat burning ending threshold 450. In an embodiment, these values are the following:

For men: Fat burning rate=4.5 mg/kg/min,
Heart rate variation=4 ms,
Heart rate=69% of heart rate maximum,
For women: Fat burning rate=4.7 mg/kg/min,
Heart rate variation=4.5 ms,
Heart rate=70% of heart rate maximum.

The corresponding values may be obtained for the 80% threshold 452 by using the fat burning rate curve 410.

In an embodiment, the fat burning rate curve 410 of parameterization of the fat burning rate curve is stored in the memory unit 212 of FIG. 2. The processing unit 110 fetches the fat burning rate curve and/or the parameters associated with the fat burning curve 410 and calculates a fat burning rate, which corresponds to the observed heart rate variation or the heart rate corresponding to the heart rate variation. The processing unit 110 may compare the observed fat burning rate with the threshold.

In an embodiment, the processing unit 110 monitors the heart rate variation and compares the heart rate variation with a threshold value, which corresponds to a fat burning rate threshold, such as the fat burn ending rate threshold 450 or the 80% fat burning rate threshold 452.

It has now been detected that the parameters having a statistically significant relation to real-time fat burning are associated to heart rate variation. A threshold having a statistically significant explanative share to the ending of fat burning (at a protocol of increasing load) can be determined especially from a fast heart rate variation parameter. This explanative share may be improved based on a threshold adjusted on the basis of the heart rate level. For example, a low heart rate variation when compared with the heart rate level is an indication of a lower fat burn level.

In an embodiment, a threshold, e.g. a FAT/FIT threshold value, can be determined and indicated to the user in a suitable manner. For example, for volume training and fat burning, the user is advised to exercise below the determined threshold value. Training over the threshold value results in a glycolytic exercise that requires recovery and increases fitness. When training around the threshold value, the user's fat burning ability may be improved and the threshold value thus moves upwards.

In an embodiment, the heart rate and heart rate variation of a user are measured and determined in context with each exercise. Next, an intensity level at which the fat burning level during the exercise becomes very low (e.g. less than 30% of the personal maximum level, i.e. the fat burning ends in practice) is detected by using a selected heart rate variation parameter. Further, an absolute highest point of fat burning may be estimated. The determined threshhold value for fat burning may be communicated to the user as a heart rate value, the overhead values of which being in an area using energy mainly glycolytically. This information may be associated to improving one's fitness (adequate metabolic stimulus).

In an embodiment, the determined threshold value for fat burning, e.g. a heart rate value, may be used as a lower limit for workload of improving one's fitness.

Many endurance athletes are forced to focus on developing their heart rate area upper limit of fat use, whereas health-oriented users, weight-watchers and fitness athletes will benefit from an area where they may safely increase the volume of their weekly targets without running the risk of loosing safe recovery. The determined threshold values may be used in training endurance athletes to determine suitable training capacities and to monitor the effects of the training. Similarly, the thresholds can be used for determining the optimum training capacities for a dieting person, for example. When heart rate values corresponding to the thresholds are known, a desired training capacity can be accurately maintained by means of continuous heart rate monitoring.

In a practical example, the user may start an exercise that is programmed to be started in a way that the workload of the user does not immediately rise to a maximum level (warm-up period). As a specific heart rate value exceeds a threshold where fat burning is determined to end or drop to a minimum level, this heart rate value is communicated to the user as an upper limit for fat burning, for example. It is also possible to indicate the user on the fact that exercising above a specific heart rate value will improve the maximum fitness level of the user. Further, endurance athletes may be advised to do a lot of exercise around this heart rate value. This will train the fat usage that is essential in an endurance performance and the heart rate value may be raised towards a greater workload level/heart rate level.

Figure 5:
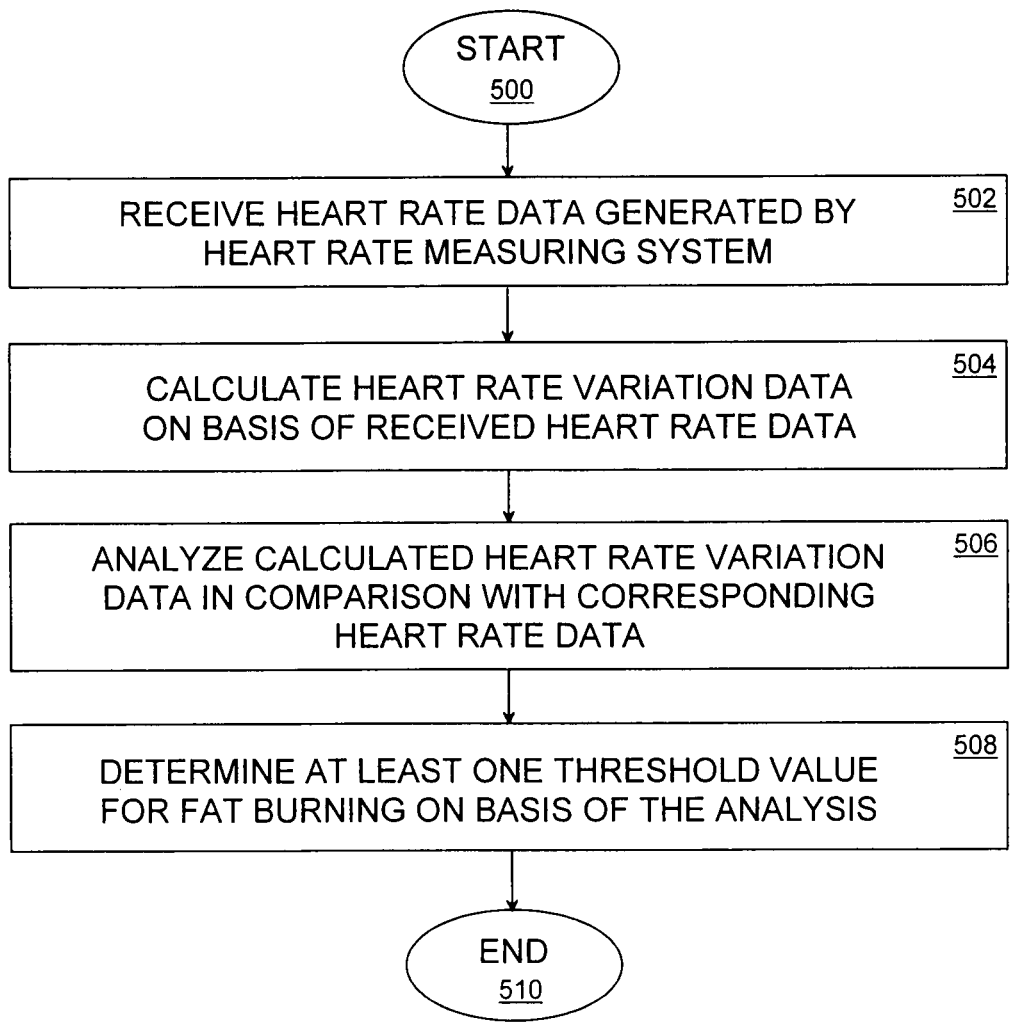
FIG. 5 shows an example of a method according to an embodiment.

FIG. 5 shows an example of a method according to an embodiment. The method starts in 500. In 502, heart rate data generated by a heart rate measuring system is received. In 504, heart rate variation data is calculated on the basis of the received heart rate data.

In 506, the calculated heart rate variation data is analysed in comparison with the corresponding heart rate data. In 508, at least one threshold value for fat burning is determined on the basis of the analysis. The method ends in 510.

The embodiments of the invention may be implemented in an electronic device comprising a processing unit including a graphic generator. The processing unit may be configured to perform at least some of the steps described in connection with the flowchart of FIG. 5 and in connection with FIGS. 1 to 4. The embodiments may be implemented as a computer program comprising instructions for executing a computer process. The computer process according to an embodiment comprises: receiving heart rate data generated by a heart rate measuring system; and calculating heart rate variation data on the basis of the received heart rate data. The process further comprises: analysing the calculated heart rate variation data in comparison with the corresponding heart rate data, and determining at least one threshold value for fat burning on the basis of the analysis.

The computer program may be stored on a computer program distribution medium readable by a computer or a processor. The computer-readable program medium may be, for example but not limited to, an electric, magnetic, optical, infrared or semiconductor system, device or transmission medium. The computer program medium may include at least one of the following media: a computer readable medium, a program storage medium, a record medium, a computer readable memory, a random access memory, an erasable programmable read-only memory, a computer readable software distribution package, a computer readable signal, a computer readable telecommunications signal, computer readable printed matter, and a computer readable compressed software package.

It will be obvious to a person skilled in the art that, as the technology advances, the inventive concept can be implemented in various ways. The invention and its embodiments are not limited to the examples described above but may vary within the scope of the claims.

The invention claimed is:

1. An electronic device, comprising:
   a receiving unit configured to receive heart rate data generated by a heart rate measuring system;
   a calculation unit configured to calculate heart rate variation data based on the received heart rate data; and
   a processing unit configured to determine at least one fat burning threshold value using the calculated heart rate variation data and a stored curve relating fat burning rate to heart rate variation.

2. The electronic device of claim 1, wherein the processing unit is further configured to determine the fat burning threshold value at which fat burning ends using the calculated heart rate variation data and the stored curve relating fat burning rate to heart rate variation.

3. The electronic device of claim 1, wherein the processing unit is further configured to provide instructions on indicating the determined at least one fat burning threshold value.

4. The electronic device of claim 1, wherein the determined at least one fat burning threshold value is at least one of: a heart rate value at a certain fat burning value, a heart rate variation value at a certain fat burning value, an upper limit at which fat burning is effective, a lower limit at which fat burning ends, a limit where fat burning starts, a percentage of the maximum fat burning ability at a certain heart rate variation level.

5. The electronic device of claim 1, wherein the processing unit is further configured to determine a ratio between carbohydrate consumption and fat burning using the calculated heart rate variation data and the stored curve relating fat burning rate to heart rate variation.

6. The electronic device of claim 1, wherein the processing unit is further configured to determine the proportion of energy that has been burned as fat using the calculated heart rate variation data and the stored curve relating fat burning rate to heart rate variation.

7. The electronic device of claim 1, wherein the processing unit is further configured to estimate a value where the maximum amount of fat is burned using the calculated heart rate variation data and the stored curve relating fat burning rate to heart rate variation.

8. The electronic device of claim 7, wherein the processing unit is further configured to estimate the value where the maximum amount of fat is burned by selecting a heart rate variation value from the stored curve relating fat burning rate to heart rate variation.

9. The electronic device of claim 1, wherein the processing unit is further configured to provide instructions on indicating at least one of: reaching the fat burning threshold value, staying below the fat burning threshold value, remaining above the fat burning threshold value, remaining in the vicinity of the fat burning threshold value.

10. A method, comprising:
    receiving heart rate data generated by a heart rate measuring system;
    calculating heart rate variation data, by a processing device, based on the received heart rate data; and
    determining, by the processing device, at least one fat burning threshold value using the calculated heart rate variation data and a stored curve relating fat burning rate to heart rate variation.

11. The method of claim 10, the method comprising determining the threshold value at which fat burning ends using the calculated heart rate variation data and the stored curve relating fat burning rate to heart rate variation.

12. The method of claim 10, the method further comprising providing instructions on indicating the determined at least one fat burning threshold value.

13. The method of claim 10, wherein the determined at least one fat burning threshold value is at least one of: a heart rate value at a certain fat burning value, a heart rate variation value at a certain fat burning value, an upper limit at which fat burning is effective, a lower limit at which fat burning ends, a limit where fat burning starts, a percentage of the maximum fat burning ability at a certain heart rate variation level.

14. The method of claim 10, the method further comprising determining a ratio between carbohydrate consumption and fat burning using the calculated heart rate variation data and the stored curve relating fat burning rate to heart rate variation.

15. The method of claim 10, the method further comprising determining the proportion of energy that has been burned as fat using the calculated heart rate variation data and the stored curve relating fat burning rate to heart rate variation.

16. The method of claim 10, the method further comprising estimating a value where the maximum amount of fat is burned using the calculated heart rate variation data and the stored curve relating fat burning rate to heart rate variation.

17. The method of claim 16, the method further comprising estimating the value where the maximum amount of fat is burned by selecting a heart rate variation value from the stored curve relating fat burning rate to heart rate variation.

18. The method of claim 10, the method further comprising providing instructions on indicating at least one of: reaching the fat burning threshold value, staying below the fat burning threshold value, remaining above the threshold value, remaining in the vicinity of the fat burning threshold value.

19. A computer-readable distribution medium encoding a computer program of instructions for executing a computer process, the process comprising:
    receiving heart rate data generated by a heart rate measuring system;
    calculating heart rate variation data on the basis of the received heart rate data; and
    determining at least one fat burning threshold value using the calculated heart rate variation data and a stored curve relating fat burning rate to heart rate variation.

20. The computer-readable distribution medium of claim 19, wherein the determined at least one fat burning threshold value is at least one of: a heart rate value at a certain fat burning value, a heart rate variation value at a certain fat burning value, an upper limit at which fat burning is effective, a lower limit at which fat burning ends, a limit where fat burning starts, a percentage of the maximum fat burning ability at a certain heart rate variation level.

21. The computer-readable distribution medium of claim 19, the process further comprising providing instructions on indicating at least one of: reaching the fat burning threshold value, staying below the fat burning threshold value, remaining above the fat burning threshold value, remaining in the vicinity of the threshold value.

22. The computer-readable distribution medium of claim 19, characterized by the distribution medium including at least one of the following media: a computer readable medium, a program storage medium, a record medium, a computer readable memory, a computer readable software distribution package, and a computer readable compressed software package.

\* \* \* \* \*